(12) United States Patent
Vertatschitsch et al.

(10) Patent No.: US 9,919,165 B2
(45) Date of Patent: Mar. 20, 2018

(54) SYSTEMS AND METHODS FOR FIDUCIAL TO PLAN ASSOCIATION

(71) Applicant: Varian Medical Systems, Palo Alto, CA (US)

(72) Inventors: Edward Vertatschitsch, San Carlos, CA (US); Raymond Kraft, Seattle, WA (US); Joseph Schumm, Seattle, WA (US); Andrea Morgan, Seattle, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 14/272,384

(22) Filed: May 7, 2014

(65) Prior Publication Data

US 2015/0320358 A1 Nov. 12, 2015

(51) Int. Cl.
*A61B 5/05* (2006.01)
*A61N 5/10* (2006.01)
(Continued)

(52) U.S. Cl.
CPC ............ *A61N 5/1067* (2013.01); *A61B 5/062* (2013.01); *A61B 5/1114* (2013.01);
(Continued)

(58) Field of Classification Search
CPC .... A61N 5/1049; A61N 5/1014; A61N 5/103; A61N 5/1031; A61N 2005/1051; A61N 2005/1059; A61B 19/54; A61B 2019/5287; A61B 2019/5437; A61B 2019/5475; A61B 6/508; A61B 6/54; A61B 6/547;
(Continued)

(56) References Cited

U.S. PATENT DOCUMENTS 3,349,242 A 10/1967 Braestrup
3,577,160 A 5/1971 White
(Continued)

FOREIGN PATENT DOCUMENTS

DE 19914455 10/2000
EP 0531081 A1 3/1993
(Continued)

OTHER PUBLICATIONS

International Search Report completed for PCT/US02/29390 dated Jan. 14, 2003, 6 pages.
(Continued)

*Primary Examiner* — Elmer Chao
(74) *Attorney, Agent, or Firm* — Perkins Coie LLP

(57) ABSTRACT

Various embodiments disclose systems and methods for tracking regions (e.g., tumor locations) within living organisms. Some embodiments provide real-time, highly accurate, low latency measurements of tumor location even as the tumor moves with internal body motions. Such measurements may be suitable for closed-loop radiation delivery applications where radiation therapy may be continuously guided to the tumor site even as the tumor moves. Particularly, the system may dynamically identify planned to actual fiducial correspondences by iterating through the possible assignment permutations. A successful permutation may be recorded and used to orient the patient during follow up treatment sessions.

18 Claims, 9 Drawing Sheets

(51) Int. Cl.
  *A61B 5/00* (2006.01)
  *A61B 5/06* (2006.01)
  *A61B 5/11* (2006.01)

(52) U.S. Cl.
  CPC .......... *A61B 5/4887* (2013.01); *A61N 5/1037* (2013.01); *A61N 5/1038* (2013.01); *A61N 2005/1051* (2013.01)

(58) Field of Classification Search
  CPC . G06T 2207/30081; G06T 2207/30204; G06F 19/3437
  See application file for complete search history.

(56) References Cited

U.S. PATENT DOCUMENTS

| | | |
|---|---|---|
| 3,967,161 A | 6/1976 | Lichtblau |
| 3,969,629 A | 7/1976 | McIntyre |
| 4,023,167 A | 5/1977 | Wahlstrom |
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson et al. |
| 4,260,990 A | 4/1981 | Lichtblau |
| 4,393,872 A | 7/1983 | Reznik et al. |
| 4,618,822 A | 10/1986 | Hansen |
| 4,633,250 A | 12/1986 | Anderson, III et al. |
| 4,643,196 A | 2/1987 | Tanaka et al. |
| 4,696,287 A | 9/1987 | Hortmann et al. |
| 4,745,401 A | 5/1988 | Montean |
| 4,787,098 A | 11/1988 | Silver |
| 4,795,995 A | 1/1989 | Eccleston et al. |
| 4,799,495 A | 1/1989 | Hawkins et al. |
| 4,909,789 A | 3/1990 | Taguchi et al. |
| 4,936,823 A | 6/1990 | Colvin et al. |
| 4,945,914 A | 8/1990 | Allen |
| 4,994,079 A | 2/1991 | Genese et al. |
| 5,018,178 A | 5/1991 | Katsumata et al. |
| 5,031,634 A | 7/1991 | Simon |
| 5,057,095 A | 10/1991 | Fabian |
| 5,062,847 A | 11/1991 | Barnes |
| 5,095,224 A | 3/1992 | Renger |
| 5,099,845 A | 3/1992 | Besz et al. |
| 5,107,862 A | 4/1992 | Fabian et al. |
| 5,142,292 A | 8/1992 | Chang |
| 5,152,776 A | 10/1992 | Pinchuk |
| 5,170,055 A | 12/1992 | Carroll et al. |
| 5,239,474 A | 8/1993 | Eaton, Jr. et al. |
| 5,325,873 A | 7/1994 | Hirschi et al. |
| 5,353,804 A | 10/1994 | Kornberg et al. |
| 5,391,199 A | 2/1995 | Ben-Haim |
| 5,409,004 A | 4/1995 | Sloan |
| 5,423,334 A | 6/1995 | Jordan |
| 5,425,367 A | 6/1995 | Shapiro et al. |
| 5,425,382 A | 6/1995 | Golden et al. |
| 5,431,161 A | 7/1995 | Ryals et al. |
| 5,446,548 A | 8/1995 | Gerig et al. |
| 5,509,900 A | 4/1996 | Kirkman |
| 5,528,651 A | 6/1996 | Leksell et al. |
| 5,545,993 A | 8/1996 | Taguchi et al. |
| 5,557,690 A | 9/1996 | O'Gorman et al. |
| 5,626,630 A | 5/1997 | Markowitz et al. |
| 5,638,819 A | 6/1997 | Manwaring et al. |
| 5,651,043 A | 7/1997 | Tsuyuki et al. |
| 5,680,106 A | 10/1997 | Schrott et al. |
| 5,697,384 A | 12/1997 | Miyawaki et al. |
| 5,707,362 A | 1/1998 | Yoon |
| 5,707,390 A | 1/1998 | Bonutti |
| 5,711,299 A | 1/1998 | Manwaring et al. |
| 5,713,847 A | 2/1998 | Howard, III et al. |
| 5,727,552 A | 3/1998 | Ryan |
| 5,731,996 A | 3/1998 | Gilbert |
| 5,733,322 A | 3/1998 | Starkebaum |
| 5,735,795 A | 4/1998 | Young et al. |
| 5,748,767 A | 5/1998 | Raab |
| 5,754,623 A | 5/1998 | Seki |
| 5,757,881 A | 5/1998 | Hughes |
| 5,764,052 A | 6/1998 | Renger |
| 5,769,861 A | 6/1998 | Vilsmeier |
| 5,810,851 A | 9/1998 | Yoon |
| 5,815,076 A | 9/1998 | Herring |
| 5,840,148 A | 11/1998 | Campbell et al. |
| 5,868,673 A | 2/1999 | Vesely |
| 5,879,297 A | 3/1999 | Haynor et al. |
| 5,910,144 A | 6/1999 | Hayashi |
| 5,928,137 A | 7/1999 | Green |
| 5,951,481 A | 9/1999 | Evans |
| 5,957,934 A | 9/1999 | Rapoport |
| 5,989,265 A | 11/1999 | Bouquet De La Joliniere et al. |
| 6,026,818 A | 2/2000 | Blair et al. |
| 6,031,533 A | 2/2000 | Peddada et al. |
| 6,059,734 A | 5/2000 | Yoon |
| 6,061,644 A | 5/2000 | Leis |
| 6,067,465 A | 5/2000 | Foo et al. |
| 6,076,008 A | 6/2000 | Bucholz |
| 6,081,238 A | 6/2000 | Alicot |
| 6,082,366 A | 7/2000 | Andra et al. |
| 6,118,848 A | 9/2000 | Reiffel |
| 6,144,875 A | 11/2000 | Schweikard et al. |
| 6,161,009 A | 12/2000 | Skurdal et al. |
| 6,198,963 B1 | 3/2001 | Haim et al. |
| 6,222,544 B1 | 4/2001 | Tarr et al. |
| 6,246,900 B1 | 6/2001 | Cosman et al. |
| 6,289,233 B1 | 9/2001 | Dumoulin et al. |
| 6,307,473 B1 | 10/2001 | Zampini et al. |
| 6,325,758 B1 | 12/2001 | Carol et al. |
| 6,353,655 B1 | 3/2002 | Siochi |
| 6,359,959 B1 | 3/2002 | Butler et al. |
| 6,360,116 B1 | 3/2002 | Jackson, Jr. et al. |
| 6,363,940 B1 | 4/2002 | Krag |
| 6,371,379 B1 | 4/2002 | Dames et al. |
| 6,377,162 B1 | 4/2002 | Delestienne et al. |
| 6,381,485 B1 | 4/2002 | Hunter et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,416,520 B1 | 7/2002 | Kynast et al. |
| 6,484,118 B1 | 11/2002 | Govari |
| 6,501,981 B1 | 12/2002 | Schweikard et al. |
| 6,510,199 B1 | 1/2003 | Hughes et al. |
| 6,526,415 B2 | 2/2003 | Smith et al. |
| 6,535,756 B1 | 3/2003 | Simon et al. |
| 6,650,930 B2 | 11/2003 | Ding |
| 6,662,036 B2 | 12/2003 | Cosman |
| 6,675,810 B2 | 1/2004 | Krag |
| 6,690,965 B1 | 2/2004 | Riaziat et al. |
| 6,698,433 B2 | 3/2004 | Krag |
| 6,702,780 B1 | 3/2004 | Gilboa et al. |
| 6,711,431 B2 | 3/2004 | Sarin et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,882,947 B2 | 4/2005 | Levin |
| 6,918,919 B2 | 7/2005 | Krag |
| 6,934,356 B1 | 8/2005 | Satheesan et al. |
| 6,937,696 B1 | 8/2005 | Mostafavi |
| 6,961,405 B2 | 11/2005 | Scherch |
| 6,977,504 B2 | 12/2005 | Wright et al. |
| 6,980,679 B2 | 12/2005 | Mostafavi et al. |
| 6,993,112 B2 | 1/2006 | Hesse |
| 6,999,555 B2 | 2/2006 | Mori |
| 6,999,819 B2 | 2/2006 | Swoyer et al. |
| 7,026,927 B2 | 4/2006 | Wright et al. |
| 7,027,707 B2 | 4/2006 | Imaki |
| 7,135,978 B2 | 11/2006 | Gisselberg et al. |
| 7,142,905 B2 | 11/2006 | Slayton et al. |
| 7,154,991 B2 | 12/2006 | Earnst et al. |
| 7,174,201 B2 | 2/2007 | Govari et al. |
| 7,176,798 B2 | 2/2007 | Dimmer et al. |
| 7,206,626 B2 | 4/2007 | Quaid, III |
| 7,206,627 B2 | 4/2007 | Abovitz et al. |
| 7,213,009 B2 | 5/2007 | Pestotnik et al. |

(56) References Cited

U.S. PATENT DOCUMENTS

| | | |
|---|---|---|
| 7,221,733 B1 | 5/2007 | Takai et al. |
| 7,241,283 B2 | 7/2007 | Putz |
| 7,280,863 B2 | 10/2007 | Shachar |
| 7,289,599 B2 | 10/2007 | Seppi et al. |
| 7,289,839 B2 | 10/2007 | Dimmer et al. |
| 7,447,643 B1 | 11/2008 | Olson et al. |
| 7,557,353 B2 | 7/2009 | Black et al. |
| 7,587,234 B2 | 9/2009 | Owens et al. |
| 7,606,405 B2 | 10/2009 | Sawyer et al. |
| 7,657,301 B2 | 2/2010 | Mate et al. |
| 7,657,302 B2 | 2/2010 | Mate et al. |
| 7,657,303 B2 | 2/2010 | Mate et al. |
| 7,684,849 B2 | 3/2010 | Wright et al. |
| 7,729,742 B2 | 6/2010 | Govari |
| 7,747,307 B2 | 6/2010 | Wright et al. |
| 7,899,513 B2 | 3/2011 | Phillips et al. |
| 8,050,774 B2 | 11/2011 | Kveen et al. |
| 8,095,203 B2 | 1/2012 | Wright et al. |
| 8,121,368 B2 | 2/2012 | Wiersma et al. |
| 8,197,494 B2 | 6/2012 | Jaggi et al. |
| 8,239,005 B2 | 8/2012 | Wright et al. |
| 2002/0049362 A1 | 4/2002 | Ding |
| 2002/0065461 A1 | 5/2002 | Cosman |
| 2002/0165443 A1 | 11/2002 | Mori |
| 2002/0183611 A1 | 12/2002 | Fishbein et al. |
| 2002/0188194 A1 | 12/2002 | Cosman |
| 2002/0193685 A1 | 12/2002 | Mate et al. |
| 2003/0002621 A1 | 1/2003 | Hughes et al. |
| 2003/0023161 A1 | 1/2003 | Govari et al. |
| 2003/0052785 A1 | 3/2003 | Gisselberg et al. |
| 2003/0070682 A1 | 4/2003 | Wilson et al. |
| 2003/0088178 A1 | 5/2003 | Owens et al. |
| 2003/0120150 A1 | 6/2003 | Govari |
| 2003/0125616 A1 | 7/2003 | Black et al. |
| 2003/0125622 A1 | 7/2003 | Schweikard et al. |
| 2003/0184285 A1 | 10/2003 | Anderson et al. |
| 2003/0192557 A1 | 10/2003 | Krag et al. |
| 2003/0206610 A1 | 11/2003 | Collins |
| 2003/0206614 A1 | 11/2003 | Kendrick et al. |
| 2003/0212412 A1 | 11/2003 | Dillard et al. |
| 2004/0013855 A1 | 1/2004 | Chen et al. |
| 2004/0019274 A1 | 1/2004 | Galloway et al. |
| 2004/0034355 A1 | 2/2004 | Govari et al. |
| 2004/0068182 A1 | 4/2004 | Misra |
| 2004/0096033 A1 | 5/2004 | Seppi et al. |
| 2004/0116804 A1 | 6/2004 | Mostafavi |
| 2004/0122311 A1 | 6/2004 | Cosman |
| 2004/0122608 A1 | 6/2004 | Levin |
| 2004/0125916 A1 | 7/2004 | Herron et al. |
| 2004/0127787 A1 | 7/2004 | Dimmer et al. |
| 2004/0133101 A1 | 7/2004 | Mate et al. |
| 2004/0133887 A1 | 7/2004 | Herle et al. |
| 2004/0158146 A1 | 8/2004 | Mate et al. |
| 2004/0176931 A1 | 9/2004 | Wright et al. |
| 2005/0059884 A1 | 3/2005 | Krag |
| 2005/0059887 A1 | 3/2005 | Mostafavi et al. |
| 2005/0077459 A1 | 4/2005 | Engler et al. |
| 2005/0085710 A1 | 4/2005 | Earnst et al. |
| 2005/0140372 A1 | 6/2005 | Wright et al. |
| 2005/0144139 A1 | 6/2005 | Zhuge et al. |
| 2005/0151649 A1 | 7/2005 | Wright et al. |
| 2005/0152495 A1 | 7/2005 | Hesse |
| 2005/0154280 A1 | 7/2005 | Wright et al. |
| 2005/0154283 A1 | 7/2005 | Wright et al. |
| 2005/0154284 A1 | 7/2005 | Wright et al. |
| 2005/0154293 A1 | 7/2005 | Gisselberg et al. |
| 2005/0195084 A1 | 9/2005 | Dimmer et al. |
| 2005/0201510 A1 | 9/2005 | Mostafavi |
| 2005/0203431 A1 | 9/2005 | Brodnick et al. |
| 2005/0234332 A1 | 10/2005 | Murphy |
| 2005/0251111 A1 | 11/2005 | Saito et al. |
| 2005/0261570 A1 | 11/2005 | Mate et al. |
| 2006/0052694 A1 | 3/2006 | Phillips et al. |
| 2006/0058648 A1 | 3/2006 | Meier et al. |
| 2006/0063999 A1 | 3/2006 | Herron et al. |
| 2006/0074301 A1 | 4/2006 | Meier et al. |
| 2006/0074302 A1 | 4/2006 | Meier et al. |
| 2006/0078086 A1 | 4/2006 | Riley et al. |
| 2006/0079764 A1 | 4/2006 | Wright et al. |
| 2006/0100509 A1 | 5/2006 | Wright et al. |
| 2006/0147100 A1 | 7/2006 | Fitzpatrick et al. |
| 2006/0173294 A1 | 8/2006 | Ein-Gal |
| 2007/0153972 A1 | 7/2007 | Fujishige et al. |
| 2007/0161884 A1 | 7/2007 | Black et al. |
| 2008/0039746 A1 | 2/2008 | Hissong et al. |
| 2008/0226149 A1 | 9/2008 | Wischmann et al. |
| 2010/0282983 A1* | 11/2010 | Wright ............... A61B 5/1127 250/491.1 |
| 2012/0138801 A1 | 6/2012 | Vanderpohl et al. |
| 2015/0085072 A1* | 3/2015 | Yan ..................... A61B 6/03 348/43 |

FOREIGN PATENT DOCUMENTS

| | | |
|---|---|---|
| FR | 2635259 | 2/1990 |
| FR | 2686499 | 7/1993 |
| JP | 8-166446 | 6/1996 |
| WO | WO-95/25475 | 9/1995 |
| WO | WO-97/12553 | 4/1997 |
| WO | WO-98/30166 | 7/1998 |
| WO | WO-98/38908 | 9/1998 |
| WO | WO-98/40026 A | 9/1998 |
| WO | WO-99/30182 | 6/1999 |
| WO | WO-99/33406 | 7/1999 |
| WO | WO-99/40869 | 8/1999 |
| WO | WO-9953966 | 10/1999 |
| WO | WO-99/58044 | 11/1999 |
| WO | WO-99/58065 | 11/1999 |
| WO | WO-00/24332 | 5/2000 |
| WO | WO-00/38579 | 7/2000 |
| WO | WO-00/51514 | 9/2000 |
| WO | WO 00/53115 | 9/2000 |
| WO | WO-00/65989 A | 11/2000 |
| WO | WO-01/034049 | 5/2001 |
| WO | WO-01/54765 | 8/2001 |
| WO | WO-02/19908 | 3/2002 |
| WO | WO-02/39917 | 5/2002 |
| WO | WO-02/39918 | 5/2002 |
| WO | WO-02/100485 A1 | 12/2002 |
| WO | WO-04/060177 | 7/2004 |
| WO | WO-04/060475 | 7/2004 |
| WO | WO-05/067792 | 7/2005 |
| WO | WO-2006002396 | 1/2006 |
| WO | WO-06/023055 | 3/2006 |
| WO | WO-2007035798 | 3/2007 |
| WO | WO-2009149409 | 12/2009 |

OTHER PUBLICATIONS

European Search Report for European Patent Application No. 03814943.1 dated Apr. 1, 2008, 8 pages.
International Search Report and Written Opinion for PCT/US03/41140 dated Jun. 1, 2007, 11 pages.
Kirsch S. et al., "Real Time Tracking of Tumor Positions for Precision Irradiation", Elsevier Science B. V., Jun. 24, 1998, pp. 262-264, 3 pages.
Final Office Action, U.S. Appl. No. 09/877,498, Applicant: Calypso Medical Technologies, Inc., dated Feb. 14, 2006, 7 pages.
Decision on Appeal, U.S. Appl. No. 09/877,498, Applicant: Calypso Medical Technologies, Inc., dated May 27, 2009, 16 pages.
Hsiao, K. "Fast Multi-Axis Tracking of Magnetically-Resonant Passive Tags: Methods and Applications," Feb. 2001, Massachusetts Institute of Technology, Dept. of Electrical Engineering and Computer Science, pp. 1-107.
International Preliminary Examination Report for PCT/US02/17876, dated Jul. 8, 2004, Applicant: Calypso Medical Technologies, Inc., 4 pages.
European Search Report for European Application No. 10185512 dated Jun. 28, 2011, 3 pages.
International Search Report and Written Opinion for PCT/US09/046494, dated Jul. 28, 2009, 10 pages.

(56) References Cited

OTHER PUBLICATIONS

European Search Report for European Application No. 05763751, Applicant: Calypso Medical, Inc., dated Feb. 21, 2008, 5 pages.
European Search Report for European Application No. 05763751, Applicant: Calypso Medical, Inc., dated Sep. 18, 2008, 5 pages.
Sharp et al., "Prediction of Respiratory Tumour Motion for Real-Time Image-Guided Radiotherapy," published Jan. 16, 2004, IPO Publishing Ltd., pp. 425-440, 16 pages.
P.G. Seiler, et al, "A Novel Tracking Technique for the Continuous Precise Measurement of Tumour Positions in Conformal Therapy," Jun. 7, 2000, IOP Publishing Ltd., Phys. Med. Biol., vol. 45, pp. N103-N110, 8 pages.
International Search Report for PCT/US05/22374 dated Apr. 25, 2007, 1 page.
Written Opinion for PCT/US05/022374 dated Apr. 25, 2007, 5 pages.
International Search Report for PCT/US05/01070 dated Jun. 21, 2005, 1 page.
Written Opinion for PCT/US05/01070 dated Jun. 21, 2005, 3 pages.
International Search Report for PCT/US05/022568 dated Feb. 16, 2007, 1 page.
Written Opinion for PCT/US05/022568 dated Feb. 16, 2007, 4 pages.
International Search Report for PCT/US06/036585 dated Jun. 23, 2008, 1 page.
Written Opinion for PCT/US06/036585 dated Jun. 23, 2008, 3 pages.
International Search Report for PCT/US09/046494 dated Jul. 28, 2009, 1 page.
Written Opinion for PCT/US09/046494 dated Jul. 28, 2009, 8 pages.
Hong, Julian C. et al., "Migration of implanted markers for image-guided lung tumor stereotactic ablative radiotherapy", Journal of Applied Clinical Medical Physics, 14, No. 2 (2013).
Jiang, Steve B. , "Radiotherapy of mobile tumors", Seminars in radiation oncology, vol. 16, No. 4, pp. 239-248, WB Saunders (2006).

* cited by examiner

SYSTEMS AND METHODS FOR FIDUCIAL TO PLAN ASSOCIATION

FIELD

Various of the disclosed embodiments relate to systems and methods for locating regions of the human body, e.g., for applying real-time treatment to cancerous tumors.

BACKGROUND

Many surgical and therapeutic procedures require an accurate, up-to-date representation of a patient's localized internal regions. For example, radiation therapy has successfully treated various cancers, including prostate cancer, lung cancer, and brain cancer, by delivering radiation to a specified region in quantified dosages. While higher doses may be more effective in disrupting the cancer, higher doses may also severely damage surrounding tissue. Similarly, dispersing the radiation into healthy regions may lessen the desired effect upon the unhealthy region. Sonic and drug delivery mechanisms may suffer similar complications.

Many prior art systems adopt a manual and often error prone means of determining the correct association. This process may involve careful tracking of fiducial identifiers during the implantation process and using this information to assign the identifiers to the corresponding measured coordinates of the fiducial at treatment planning time. Such approaches are error-prone and often have deleterious consequences.

Accordingly, there is a need for accurate, efficient, and reliable systems and methods for associating implanted fiducials with their planned counterparts.

BRIEF DESCRIPTION OF THE DRAWINGS

The techniques introduced here may be better understood by referring to the following Detailed Description in conjunction with the accompanying drawings, in which like reference numerals indicate identical or functionally similar elements.

Figure 1:
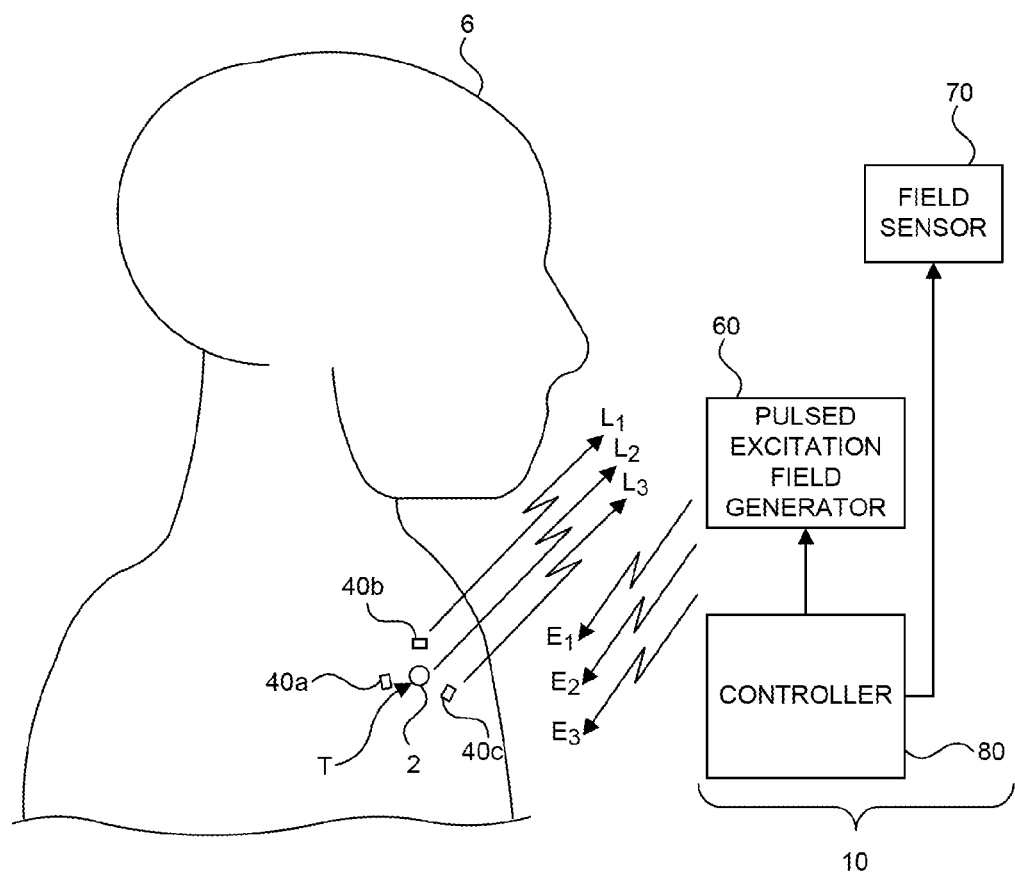
FIG. 1 is a side view schematically illustrating an example localization system and a plurality of markers implanted in a patient as may occur in some embodiments.

The headings provided herein are for convenience only and do not necessarily affect the scope or meaning of the claimed embodiments. Further, the drawings have not necessarily been drawn to scale. For example, the dimensions of some of the elements in the figures may be expanded or reduced to help improve the understanding of the embodiments. Similarly, some components and/or operations may be separated into different blocks or combined into a single block for the purposes of discussion of some of the embodiments. Moreover, while the various embodiments are amenable to various modifications and alternative forms, specific embodiments have been shown by way of example in the drawings and are described in detail below. The intention, however, is not to limit the particular embodiments described. On the contrary, the embodiments are intended to cover all modifications, equivalents, and alternatives falling within the scope of the disclosed embodiments as defined by the appended claims.

DETAILED DESCRIPTION

Overview

Various embodiments disclose systems and methods for tracking tumors within living organisms. Some embodiments provide real-time, highly accurate, low latency measurements of tumor location even as the tumor moves with internal body motions. Such measurements may be suitable for closed-loop radiation delivery applications where radiation therapy may be continuously guided to the tumor site even as the tumor moves. Tumor motion may be associated with periodic motion (e.g., respiratory, cardiac) or aperiodic motion (e.g., gross patient motion, internal bowel motion). Various embodiments facilitate accurate radiation delivery to tumor sites exhibiting significant motion, e.g., lung, breast, and liver tumors.

Various examples of the disclosed techniques will now be described in further detail. The following description provides specific details for a thorough understanding and enabling description of these examples. One skilled in the relevant art will understand, however, that the techniques discussed herein may be practiced without many of these details. Likewise, one skilled in the relevant art will also understand that the techniques can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the embodiments. Indeed, certain terms may even be emphasized below; however, any terminology intended to be interpreted in any restricted manner will be overtly and specifically defined as such in this section.

Example System

FIG. 1 is a block diagram of an example location determination system. For full details concerning such a system, the reader is referred to U.S. patent application Ser. No. 11/166,801 titled "SYSTEMS AND METHODS FOR REAL TIME TRACKING OF TARGETS IN RADIATION THERAPY AND OTHER MEDICAL APPLICATIONS" filed Jun. 24, 2005, the contents of which are incorporated by reference herein in their entirety for all purposes. Though examples are discussed herein with respect to human patients, one will recognize that many techniques may be applied in a veterinary context as well.

The localization system 10 and the markers 40a-c may be used to determine the location of the target 2 before, during and after radiation sessions. More specifically, the localization system 10 may determine the locations of the markers 40a-c and provide objective target position data to a memory, user interface, linear accelerator and/or other device in real time during setup, treatment, deployment, simulation, surgery, and/or other medical procedures. In some embodiments of the localization system, "real time" means that indicia of objective coordinates are provided to a user interface at (a) a sufficiently high refresh rate (i.e., frequency) such that pauses in the data are generally not humanly discernable and (b) a sufficiently low latency so as to be at least substantially contemporaneous with the measurement of the location signal. The high refresh rate may also be used to accurately sample and display relevant features of the target trajectory, e.g. in relation to a boundary, as discussed herein. In other embodiments, "real time" is defined by higher frequency ranges and lower latency ranges for providing the objective data to a radiation delivery device, or in still other embodiments "real time" is defined as providing objective data responsive to the location of the markers (e.g., at a frequency that adequately tracks the location of the target in real time and/or a latency that is substantially contemporaneous with obtaining position data of the markers). Accordingly, one will construe the phrase in the context in which it is discussed.

In this example, the localization system 10 includes an excitation source 60 (e.g., a pulsed magnetic field generator), a sensor assembly 70, and a controller 80 coupled to both the excitation source 60 and the sensor assembly 70. The excitation source 60 generates an excitation energy to energize at least one of the markers 40a-c in the patient 6 (FIG. 1). The excitation source 60 may produce a pulsed magnetic field at different frequencies. For example, the excitation source 60 may frequency multiplex the magnetic field at a first frequency $E_1$ to energize the first marker 40a, a second frequency $E_2$ to energize the second marker 40b, and a third frequency $E_3$ to energize the third marker 40c. In response to the excitation energy, the markers 40a-c generate location signals $L_1$, $L_2$, $L_3$ at unique response frequencies. More specifically, in this example the first marker 40a generates a first location signal $L_1$ at a first frequency in response to the excitation energy at the first frequency $E_1$, the second marker 40b generates a second location signal $L_2$ at a second frequency in response to the excitation energy at the second frequency $E_2$, and the third marker 40c generates a third location signal $L_3$ at a third frequency in response to the excitation energy at the third frequency $E_3$. In an alternative embodiment with two markers, the excitation source generates the magnetic field at frequencies $E_1$ and $E_2$, and the markers 40a-b generate location signals $L_1$ and $L_2$, respectively.

The sensor assembly 70 can include a plurality of coils to sense the location signals $L_1$, $L_2$, $L_3$ from the markers 40a-c. The sensor assembly 70 can be a flat panel having a plurality of coils that are at least substantially coplanar relative to each other. In other embodiments, the sensor assembly 70 may be a non-planar array of coils.

The controller 80 includes hardware, software or other computer-operable media containing instructions that operate the excitation source 60 to multiplex the excitation energy at the different frequencies $E_1$, $E_2$, $E_3$. For example, the controller 80 causes the excitation source 60 to generate the excitation energy at the first frequency $E_1$ for a first excitation period, and then the controller 80 causes the excitation source 60 to terminate the excitation energy at the first frequency $E_1$ for a first sensing phase during which the sensor assembly 70 senses the first location signal $L_1$ from the first marker 40a without the presence of the excitation energy at the first frequency $E_1$. The controller 80 then causes the excitation source 60 to: (a) generate the second excitation energy at the second frequency $E_2$ for a second excitation period; and (b) terminate the excitation energy at the second frequency $E_2$ for a second sensing phase during which the sensor assembly 70 senses the second location signal $L_2$ from the second marker 40b without the presence of the second excitation energy at the second frequency $E_2$. The controller 80 then repeats this operation with the third excitation energy at the third frequency $E_3$ such that the third marker 40c transmits the third location signal $L_3$ to the sensor assembly 70 during a third sensing phase. As such, the excitation source 60 wirelessly transmits the excitation energy in the form of pulsed magnetic fields at the resonant frequencies of the markers 40a-c during excitation periods, and the markers 40a-c wirelessly transmit the location signals $L_1$, $L_2$, $L_3$ to the sensor assembly 70 during sensing phases. It will be appreciated that the excitation and sensing phases can be repeated to permit averaging of the sensed signals to reduce noise.

The computer-operable media in the controller 80, or in a separate signal processor, or other computer also includes instructions to determine the absolute positions of each of the markers 40a-c in a three-dimensional reference frame. Based on signals provided by the sensor assembly 70 that correspond to the magnitude of each of the location signals $L_1$, $L_2$, $L_3$, the controller 80 and/or a separate signal processor may calculate the absolute location coordinates of each of the markers 40a-c in the three-dimensional reference frame and/or the 2-dimensional orientation of the markers. The absolute location coordinates of the markers 40a-c may be objective data that can be used to calculate the coordinates of the target in the reference frame. When multiple markers are used, the rotation of the target can also be calculated.

The localization system 10 and at least one of a marker 40 enables real time tracking of the target 2 relative to the machine isocenter or another external reference frame outside of the patient during treatment planning, set up, radiation sessions, and at other times of the radiation therapy process. In some embodiments, real time tracking refers to the collection of position and/or orientation data of the markers, determining the locations of the markers in an external reference frame, and providing an objective output in the external reference frame that is responsive to the location of the markers. The objective output is provided at a frequency that adequately tracks the target in real time and/or a latency that is at least substantially contemporaneous with collecting the position data (e.g., within a generally concurrent period of time). In some embodiments, the objective output consists of the location of the target 2 in a reference frame external to the patient (e.g., the operating room). In some real time tracking embodiments, the objective output is provided at a plurality of times during an "on-beam" period (e.g., 2, 5, 10 or more times while the beam is on).

For example, several embodiments of real time tracking are defined as determining the locations of the markers and calculating the location of the target relative to the machine isocenter at (a) a sufficiently high frequency so that pauses in representations of the target location at a user interface do not interrupt the procedure or are readily discernable by a human (e.g., sufficiently high frequency that the trajectory of the target is adequately sampled), and (b) a sufficiently low latency to be at least substantially contemporaneous with the measurement of the location signals from the markers. Alternatively, real time means that the location system 10 calculates the absolute position of each individual marker 40 and/or the location of the target at a periodicity of 1 ms to 5 seconds, or in many applications at a periodicity of approximately 10-100 ms, or in some specific applications at a periodicity of approximately 20-50 ms. In applications for user interfaces, for example, the periodicity can be 12.5 ms (i.e., a frequency of 80 Hz), 16.667 ms (60 Hz), 20 ms (50 Hz), and/or 50 ms (20 Hz).

Alternatively, real time tracking can further mean that the location system 10 provides the absolute locations of the markers 40 and/or the target 2 to a memory device, user interface, linear accelerator or other device within a latency of 10 ms to 5 seconds from the time the localization signals were transmitted from the markers 40. In more specific applications, the location system generally provides the locations of the markers 40 and/or target 2 within a latency of about 20-50 ms. The location system 10 accordingly provides real time tracking to monitor the position of the markers 40 and/or the target 2 with respect to an external reference frame in a manner that is expected to enhance the efficacy of radiation therapy because higher radiation doses can be applied to the target and collateral effects to healthy tissue can be mitigated.

Alternatively, real-time tracking can further be defined by the tracking error. Measurements of the position of a moving target are subject to motion-induced error, generally referred to as a tracking error. According to aspects of various of the present embodiments, the localization system 10 and at least one marker 4 enable real time tracking of the target 2 relative to the machine isocenter or another external reference frame with a tracking error that is within clinically meaningful limits.

Tracking errors may arise due to two limitations exhibited by any practical measurement system, specifically (a) latency between the time the target position is sensed and the time the position measurement is made available, and (b) sampling delay due to the periodicity of measurements. For example, if a target is moving at 5 cm/s and a measurement system has a latency of 200 ms, then position measurements will be in error by 1 cm. The error in this example is due to latency alone, independent of any other measurement errors, and is simply due to the fact that the target has moved between the time its position is sensed and the time the position measurement is made available for use. If this exemplary measurement system further has a sampling periodicity of 200 ms (i.e., a sampling frequency of 5 Hz), then the peak tracking error increases to 2 cm, with an average tracking error of 1.5 cm.

For a real time tracking system to be useful in medical applications, it is desirable to keep the tracking error within clinically meaningful limits. For example, in a system for tracking motion of a tumor in a lung for radiation therapy, it may be desirable to keep the tracking error within 5 mm. In some embodiments, the system may ensure that the error is less than 2 mm and that tracking error will be in the range of 1 mm. Acceptable tracking errors may be smaller when tracking other organs for radiation therapy. In accordance with aspects of various embodiments, real time tracking refers to measurement of target position and/or rotation with tracking errors that are within clinically meaningful limits.

The system described herein uses one or more markers to serve as registration points to characterize target location, rotation, and motion. In accordance with aspects of various embodiments, the markers may have a substantially fixed relationship with the target. If the markers did not have a substantially fixed relationship with the target another type of tracking error would be incurred. This generally requires the markers to be fixed or implanted sufficiently close to the target in order that tracking errors be within clinically meaningful limits, thus, the markers may be placed in tissue or bone that exhibits representative motion of the target. For example, with respect to the prostate, tissue that is representative of the target's motion would include tissue in close proximity or adjacent to the prostate. In the example application of tumor treatment in a prostate, the fiducials may be placed in the gland itself as the gland itself may be more rigid than the surrounding tissue. However, the prostate gland, the fiducials implanted in the gland, and the tumor sites within the gland may all move together. With respect to the prostate, tracking tissue that is a 5 cm radial distance from the target would provide representative motion that is clinically useful to the motion of the target. In accordance with alternative target tracking locations, the radial distance may be greater or lesser. Fiducials inside a prostate gland may be situated less than ~2 cm from the tumor target.

According to various embodiments, the marker motion may be a fiducial for the motion of the target. Accordingly, the marker is placed such that it moves in direct correlation to the target being tracked. Depending on the target being tracked, the direct correlation relationship between the target and the marker will vary. For example, in long bones, the marker may be placed anywhere along the bone to provide motion that directly correlates to target motion in the bone. With respect to soft tissue that moves substantially in response to the bony anatomy, for example, the head and neck, the marker may be placed in a bite block to provide fiducial motion in direct correlation with target motion. With respect to soft tissue and as discussed in detail above, the target may be placed in adjacent soft tissue to provide a fiducial having direct correlation to target motion.

Figure 2:
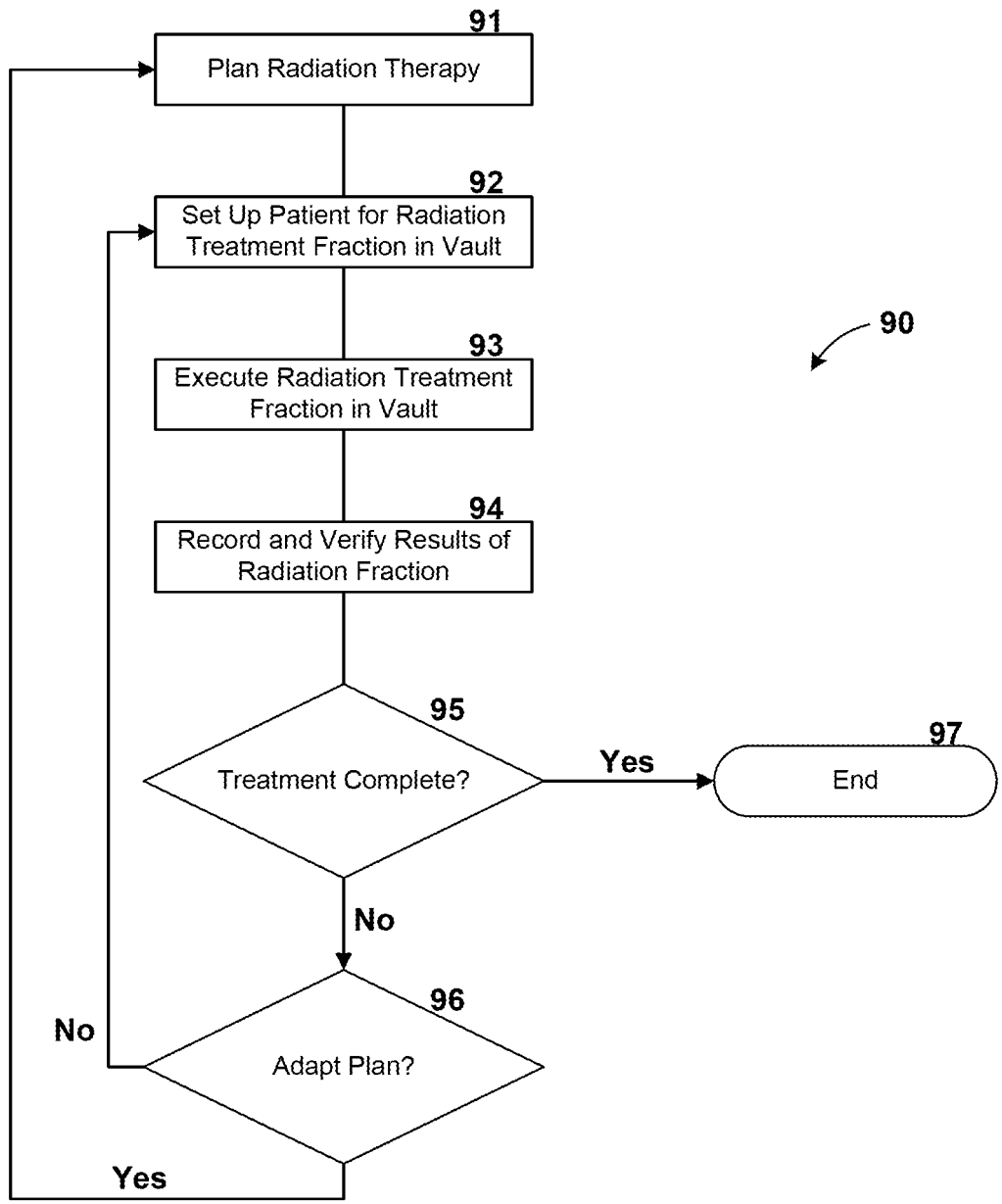
FIG. 2 is a flow diagram illustrating several aspects and uses of real time tracking to monitor the location and the status of the target as may occur in some embodiments.

FIG. 2 is a flow diagram illustrating several aspects and uses of real time tracking to monitor the location and the status of the target as may occur in some embodiments. In this embodiment, an integrated method 90 for radiation therapy includes a radiation planning procedure 91 that determines the plan for applying the radiation to the patient over a number of radiation fractions. The radiation planning procedure 91 may include an imaging stage in which images of a tumor or other types of targets are obtained using X-rays, CT, MRI, or ultrasound imaging. The images may be analyzed by a person to measure the relative distances between the markers and the relative position between the target and the markers. The coordinates of the tumor can be determined in a similar manner to ascertain the offset between the marker and the target.

The radiation planning procedure 91 can also include tracking the targets using the localization system 10 in an observation area separate from the imaging equipment. The markers 40 can be tracked to identify changes in the configuration (e.g., size/shape) of the target over time and to determine the trajectory of the target caused by movement of the target within the patient (e.g., simulation). For many treatment plans, the computer does not need to provide objective output data of the marker or target locations to a user in real time, but rather the data can be recorded in real time. Based on the images obtained during the imaging stage and the additional data obtained by tracking the markers using the localization system 10 in a simulation procedure, a treatment plan is developed for applying the radiation to the target.

The localization system 10 and the markers 40 enable an automated patient setup process for delivering the radiation. After developing a treatment plan, the method 90 includes a setup procedure 92 in which the patient is positioned on a movable support table so that the target and markers are generally adjacent to the sensor assembly. As described above, the excitation source is activated to energize the markers, and the sensors measure the strength of the signals from the markers. The computer controller may then (a) calculate objective values of the locations and/or orientations of the markers and the target relative to the machine isocenter, and (b) determine an objective offset value between the position of the target and the machine isocenter. The objective offset values can be provided to a user interface that displays the vertical, lateral and longitudinal offsets of the target relative to the machine isocenter. A user interface may, additionally or instead, display target rotation.

One aspect of several embodiments of the localization system 10 is that the objective values are provided to the user interface or other device by processing the position data from the field sensor 70 in the controller 80 or other computer without human interpretation of the data received by the field sensor 70. If the offset value is outside of an acceptable range, the computer automatically activates the control system of the support table to move the tabletop relative to the machine isocenter until the target isocenter is coincident with the machine isocenter. The computer controller generally provides the objective output data of the offset to the table control system in real time as defined above. For example, because the output is provided to the radiation delivery device, it can be with a low periodicity (1-20 ms) and low latency (10-50 ms). If the output data is provided to a user interface in addition to or in lieu of the table controller, it can be with relatively higher periodicity (20-50 ms) and higher latency (50-200 ms).

In one embodiment, the computer controller also determines the position and orientation of the markers relative to the position and orientation of simulated markers. The locations of the simulated markers may be selected so that the target will be at the machine isocenter when the real markers are at the selected locations for the simulated markers. If the markers are not properly aligned and oriented with the simulated markers, the support table is adjusted as needed for proper marker alignment. This marker alignment properly positions the target along six dimensions, namely X, Y, Z, pitch, yaw, and roll. Accordingly, the patient is automatically positioned in the correct position and rotation relative to the machine isocenter for precise delivery of radiation therapy to the target.

Referring back to FIG. 2, the method 90 further includes a radiation session 93. An automated process may be used in which the localization system 10 tracks the target during the radiation session 93 and controls the radiation delivery device 20 according to the offset between target and the machine isocenter. For example, if the position of the target is outside of a permitted degree or range of displacement from the machine isocenter, the localization system 10 sends a signal to interrupt the delivery of the radiation or prevent initial activation of the beam. In another embodiment, the localization system 10 sends signals to automatically reposition a tabletop 27 and the patient 6 (e.g., as a unit) so that the target isocenter remains within a desired range of the machine isocenter during the radiation session 93 even if the target moves. In still another embodiment, the localization system 10 sends signals to activate the radiation only when the target is within a desired range of the machine isocenter (e.g., gated therapy). In the case of treating a target in the lung, one embodiment of gated therapy includes tracking the target during inspiration/expiration, having the patient hold his/her breath at the end of an inspiration/expiration cycle, and activating the beam 21 when the computer 80 determines that the objective offset value between the target and the machine isocenter is within a desired range. Accordingly, the localization system enables dynamic adjustment of the beam in real time while irradiating the patient. This is expected to ensure that the radiation is accurately delivered to the target without requiring a large margin around the target.

The localization system provides the objective data of the offset and/or rotation to the linear accelerator and/or the patient support table in real time as defined above. For example, as explained above with respect to automatically positioning the patent support table during the setup procedure 92, the localization system generally provides the objective output to the radiation delivery device at least substantially contemporaneously with obtaining the position data of the markers and/or at a sufficient frequency to track the target in real time. The objective output, for example, can be provided at a short periodicity (1-20 ms) and a low latency (10-20 ms) such that signals for controlling the beam 21 can be sent to the radiation delivery device 20 in the same time periods during a radiation session. In the case of terminating or activating the radiation beam, or adjusting the leaves of a beam collimator, it is generally desirable to maximize the refresh rate and minimize the latency. In some embodiments, therefore, the localization system may provide the objective output data of the target location and/or the marker locations at a periodicity of 10 ms or less and a latency of 10 ms or less.

The method 90 further includes a verification procedure 94 in which the real time objective output data from the radiation session 93 is compared to the status of the parameters of the radiation beam. For example, the target locations can be correlated with the beam intensity, beam position, and collimator configuration at corresponding time intervals during the radiation session 93. This correlation can be used to determine the dose of radiation delivered to discrete regions in and around the target. This information can also be used to determine the effects of radiation on certain areas of the target by noting changes in the target configuration or the target trajectory.

The method 90 can further include a first decision (Block 95) in which the data from the verification procedure 94 is analyzed to determine whether the treatment is complete. If the treatment is not complete, the method 90 further includes a second decision (Block 96) in which the results of the verification procedure are analyzed to determine whether the treatment plan should be revised to compensate for changes in the target. If revisions are necessary, the method can proceed with repeating the planning procedure 91. On the other hand, if the treatment plan is providing adequate results, the method 90 can proceed by repeating the setup procedure 92, radiation session 93, and verification procedure 94 in a subsequent fraction of the radiation therapy.

The localization system 10 provides several features, either individually or in combination with each other, that enhance the ability to accurately deliver high doses of radiation to targets within tight margins. For example, many embodiments of the localization system use leadless markers that are implanted in the patient so that they are substantially fixed with respect to the target. The markers accordingly move either directly with the target or in a relationship proportional to the movement of the target. As a result, internal movement of the target caused by respiration, organ filling, cardiac functions, or other factors can be identified and accurately tracked before, during and after medical procedures. Moreover, many aspects of the localization system 10 use a non-ionizing energy to track the leadless markers in an external, absolute reference frame in a manner that provides objective output. In general, the objective output is determined in a computer system without having a human interpret data (e.g., images) while the localization system 10 tracks the target and provides the objective output. This significantly reduces the latency between the time when the position of the marker is sensed and the objective output is provided to a device or a user. For example, this enables an objective output responsive to the location of the target to be provided at least substantially contemporaneously with collecting the position data of the marker. The system also effectively eliminates inter-user variability associated with subjective interpretation of data (e.g., images).

Plan Correspondence Overview

As discussed above, fiducials may be used to track internal items, e.g., tumors. The fiducial locations may be more readily measureable than the item itself Such fiducials may be external to the body or they may be internally implanted. In some embodiments, imaging may be used to determine the relationship between these fiducials and the tumor at planning time. Some embodiments may determine an association between measured fiducials and plan-identified fiducials. This association may be used, e.g., for subsequent tumor tracking when there is more than a single fiducial. The number of fiducials in the plan may differ from the number measured.

Some embodiments contemplate an automated means for evaluating some or all possible associations between planned and measured fiducials, as well as identifying the most likely correct association between them. Some embodiments consider the association that minimizes an objective function comprising a collection of point registration metrics to be the "most correct" one. The system may rank all associations and characterize them as "recommended", "acceptable", and "unacceptable". For example, "Unacceptable" may indicate that an association rotation exceeds a maximum allowed rotation (e.g., 60 deg). "Recommended" may indicate that an association uniquely satisfies, across all possible associations, both a maximum fiducial registration error (FRE) limit and a rotation less than specified limits. For example, an FRE limit may be allowed to be in the range of 0.01 to 0.4 cm (typically 0.2 cm), and a rotation limit may be allowed to be in the range of 1 to 45 deg (typically 10 deg). "Acceptable" may be used for all other associations.

The characterization may be a function of the various registration metrics and whether or not a clearly superior association presents itself.

Various embodiments free the clinician from a manual and error-prone bookkeeping of the fiducials, substituting a highly efficient, accurate, and process susceptible to verification. Automatic evaluation of all possible associations between planned and measured fiducials may facilitate more comprehensive tracking assessment, yielding the greatest probability of identifying the correct association. The automatic classification and ranking of all associations facilitates faster review and verification. Automatic classification may also facilitate computing associations where the number of plan fiducials differs from the number of measured fiducials. Additionally, the graphical reassessment, per patient treatment session, and fiducial association metrics provide further verification of an appropriate deployment in a human-readable manner.

In some embodiments, instances where the number of planned and measured fiducials differ are not uncommon. The capability to accommodate this situation gives the user an efficient means of identifying which measured fiducial is missing in the plan, or which plan fiducial is not measureable. Degenerate geometries may also not be uncommon, and may include 2-fiducial geometries as well as nearly collinear 3-fiducial geometries. In these instances, a full and unique 3DOF rotation estimate may either not be possible or not straightforward to associate with goodness of fit. For degenerate geometries, the system may compute single degree of freedom rotations that may be incorporated into the same scoring system utilized for normal geometries.

Figure 3:
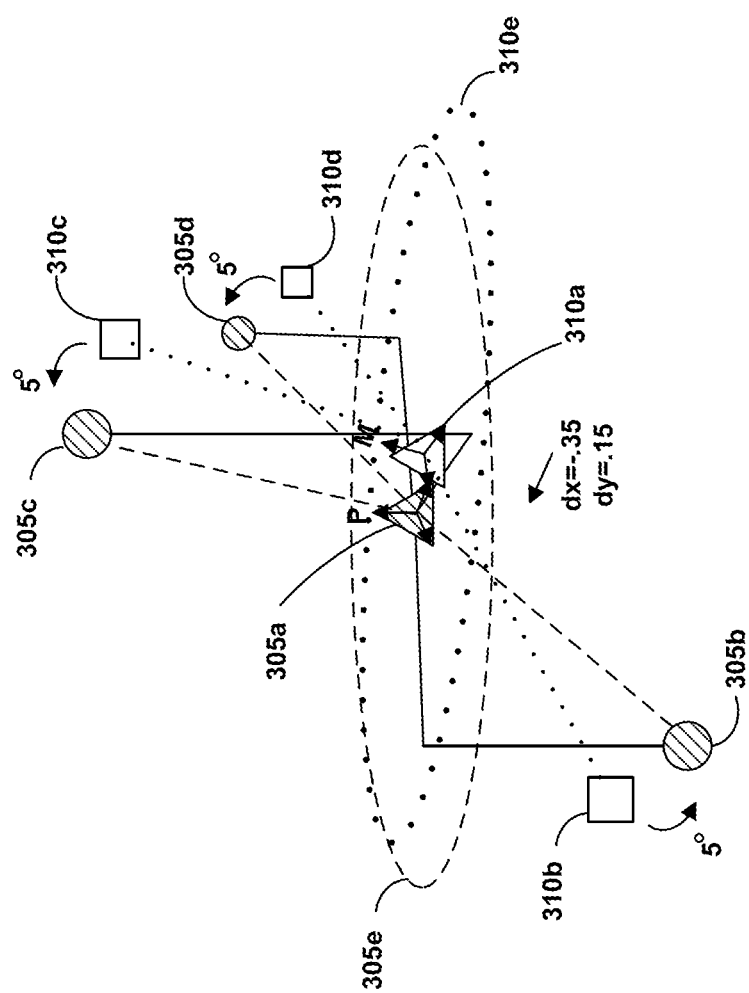
FIG. 3 is a geometric idealization of the plan-to-fiducial-measurement correspondence as may be determined in some embodiments.

FIG. 3 is a geometric idealization of the plan-to-fiducial-measurement correspondence as may be determined in some embodiments. For example, an operator/clinician may initially decide that the fiducials should be placed in "planned" positions 305$b$-$d$ within the patient's body, having centroid 305$a$ at the indicated position. This planned position and orientation may correspond to an axis with plane 305$e$. This plane may be designed for a particular patient's physical dimensions, treatment plan, disease context, etc.

The plane 305$e$ depicted in this figure is merely for ease of viewer comprehension. One will appreciate, e.g., that the plane 305$e$ reflects a "planning" coordinate reference frame P (e.g., a three-dimensional basis) associated with the planning positions. The planned fiducial positions 305$b$-$d$ may be described with respect to this planning coordinate reference frame P. In some embodiments, the reference frame may correspond to the reference frame of a CT imager.

However, during actual surgical implantation of the fiducials, the fiducials may be placed at the positions 310$b$-$d$, with centroid 310$a$. Relative to the planned orientation plane 305$e$, the actual fiducials may instead be oriented relative to an actual "measurement" coordinate reference frame M, represented by plane 310e. The measured fiducial positions 310$b$-$d$ may be captured with respect to this measurement coordinate reference frame M, e.g., a machine fixed frame (e.g., IEC-61217).

As discussed above, each of the fiducials associated with positions 310$b$-$d$ may be associated with a unique frequency. Where the planned fiducial positions 305$b$ corresponds to actual fiducial position 310$b$, 305$c$ to 310$c$, and 305$d$ to 310$d$, the actual and planned positions may be overlapped by performing a translation (dx=−0.35, dy=0.15) to the actual positions and a rotation about the overlaid centroids of 5 degrees (one will recognize that this is merely an example with N=3 fiducials and that variations with more/less fiducials and different orientations are contemplated).

However, the operator may have mistakenly switched the fiducials during implantation. For example, the fiducial (and corresponding frequency) intended for position 305$b$ may instead be switched with the fiducial intended for position 305$c$ and vice versa. Accordingly, where the system expects the fiducial frequency associated with position 310$b$ to be received from the fiducial at position 305$b$, considerable confusion may result from the disparity. Multiple rotations and translations may be attempted, but ultimately no suitable correspondence may be determined between the planned placement and the actual placement. Accordingly, various of the disclosed embodiments seek to remedy this problem.

For example, given the position values in the planned P and measured coordinate reference frames M, various embodiments determine a transformation T by optimizing an objective function. The transformation T may be applied to the planned coordinate reference frame P to produce optimal alignment with the measured reference frame M. This transformation may have associated with it a corresponding rigid body rotation and translation. Such transformations may be captured as 4×4 matrices using homogeneous coordinates in some embodiments.

Plan Correspondence Processes

Figure 4:
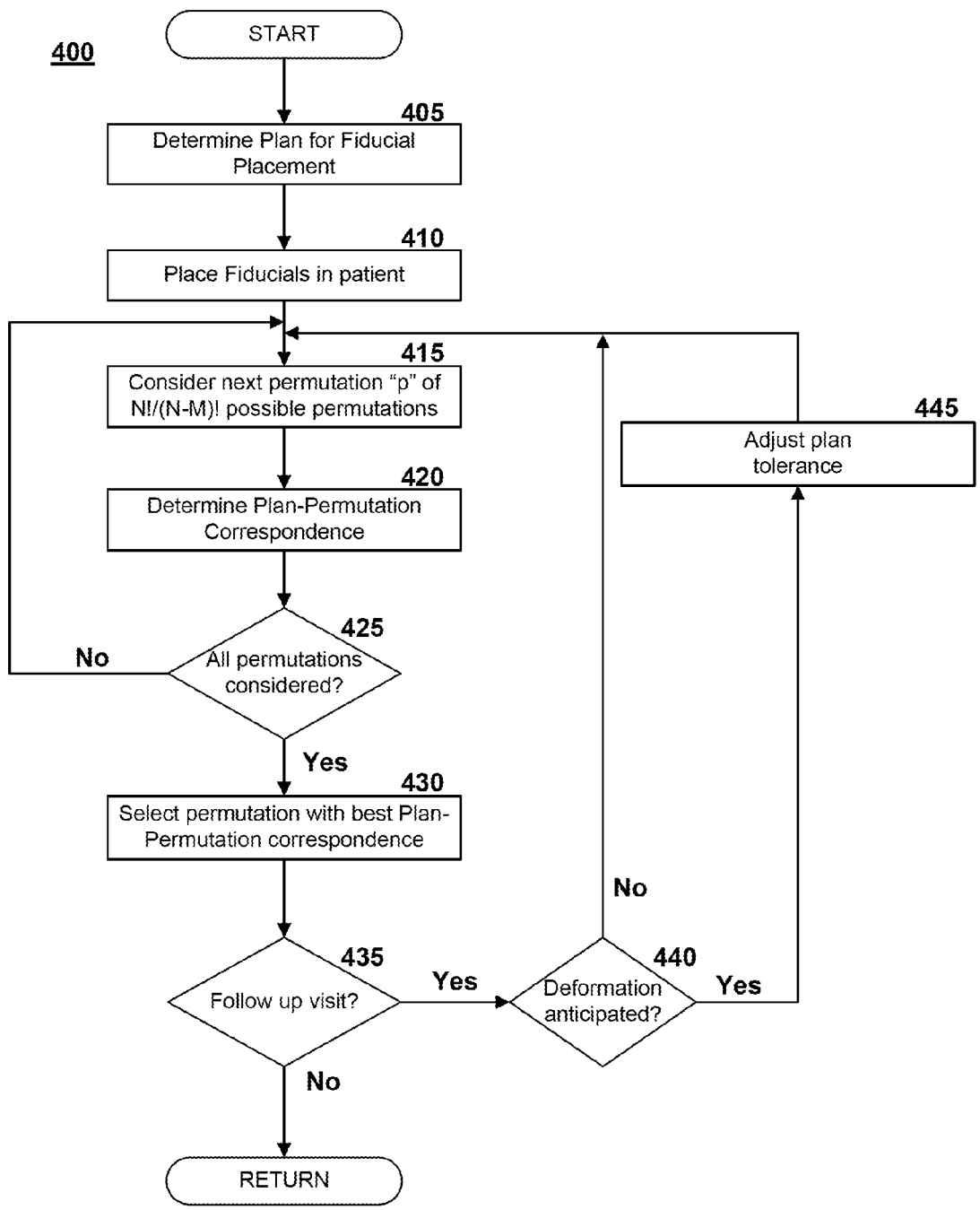
FIG. 4 is a flow diagram depicting a general process for implanting, associating, and reusing fiducials as may occur in some embodiments.

FIG. 4 is a flow diagram depicting a general process 400 for implanting, associating, and reusing fiducials as may occur in some embodiments. At block 405, the operator (e.g., a surgeon) may determine a plan for fiducial placement. At block 410, each of the N fiducials may be physically placed within the patient.

At block 415, the system may associated N planned fiducials with M magnetically measured fiducials and corresponding frequencies. Accordingly, N!/(N−M)! permutations may be considered. For example, with reference to FIG. 3 (where N=3 and M=3) the system may consider each of the six possible permutations (e.g., assuming, as a first permutation, that position 310b was intended for position 305b, 310c for 305c, and 310d for 305d; in a second permutation, assuming that position 310b was intended for position 305c, 310c for 305b, and 310d for 305d; etc.).

Figure 5:
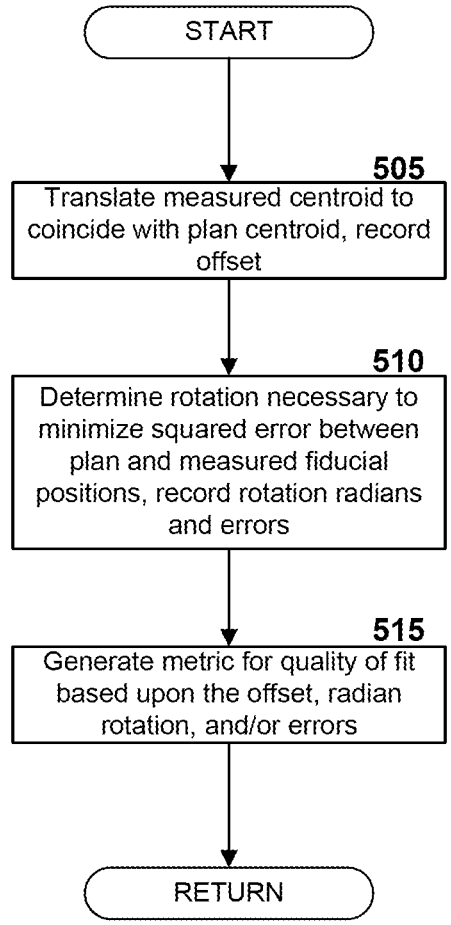
FIG. 5 is a flow diagram depicting a metric for assessing plan-to-fiducial-measurement correspondence as may occur in some embodiments.

At block 420, the system may determine the plan-permutation correspondence, e.g., using the process discussed herein at FIG. 5. The plan-permutation correspondence may be a metric based on the weighted sum of the translations and rotations necessary to minimize the least-squared error between each of the intended corresponding plan-actual fiducial positions (and may include the errors themselves in the weighting). Variations will readily be recognized based upon the representation (e.g., correspondence via quaternion or tensor representations may rely on different measures than Cartesian translations and rotations).

If all permutations have been considered at block 425, the system and/or operator may then select the permutation providing the best Plan-Permutation correspondence score. This would imply that the frequency assignments for this permutation correspond to the placement desired during the planning phase.

In some embodiments, the fiducials may be permanently placed within the patient and used during follow up treatments. Some embodiments anticipate that user physiology may change with time and/or treatment. Accordingly, during a follow up visit 435, the system and/or operator may anticipate deformations and adjust the plan 445 accordingly. For example, rather than adjust the original plan positions, the system may increase tolerances permitted for the permutation selection. If a tumor is expected to decrease in size with treatment, then the system may not object if the fiducial positions are closer in proximity with successive treatments.

FIG. 5 is a flow diagram depicting a metric for assessing plan-to-fiducial-measurement correspondence as may occur in some embodiments, e.g., as may be applied at block 420. At block 505, the system may translate the measured, actual fiducials' centroid to coincide with the position of the plan centroid and record the offset translation "offset" (e.g., the Euclidean distance).

At block 510, the system may determine the rotation "rotation" necessary to minimize the error "error" (e.g., the measurement error weighted Euclidean distance) between the plan and measured fiducial positions for each fiducial pair in the permutation. Some embodiments may consider multiple rotational degrees of freedom (e.g., Euler angles, quaternions, axis-angle, etc.).

At block 510, the system may generate a metric based on the determined values. Each of the values may be weighted based upon their relevance in a given context. Thus, the metric may take the form:

$$\text{metric value} = w_{offset} * \text{offset} + w_{rotation} * \text{rotation} + w_{error} * \sum_{n=1}^{N} error_n$$

In some embodiments, the metric may be a p-norm computation $$\text{metric value} = w_{offset} * \text{offset} + w_{rotation} * \text{rotation} + w_{error} * \left(\sum_{n=1}^{N} |error_n|^p\right)^{\frac{1}{p}}$$

where p is the desired norm metric. In some embodiments p=2 may be used, which corresponds with the standard Procrustes fit objective function, yielding an RMS metric associated with the fiducial registration error. Larger p values may be chosen to increase metric sensitivity to large deviations, while smaller values (i.e. 1) may reduce sensitivity to outlying numbers of fiducials. The value of p may be chosen to match that of the objective function minimized to compute the planned-to-measured fit.

In some embodiments, the fiducials may themselves be preferentially weighted with fiducial weights $wf_n$ in accordance with a particular system implementation (e.g., a separate weight wf for each n of the N fiducials).

$$\text{metric value} = $$

$$w_{offset} * \text{offset} + w_{rotation} * \text{rotation} + w_{error} * \left(\sum_{n=1}^{N} |wf_n * error_n|^p\right)^{\frac{1}{p}}$$

Some embodiments may rely only upon the summed error term in the above equations, or upon other of the individual components in the summation to produce a metric value (e.g., only the final error, rather than the translations and rotations, is considered).

One will recognize multiple variations of the above examples. For example, the rotation may be defined as the maximum rotation of an Euler angle triplet. In some embodiments, the rotation may be defined as the single angle component of an axis-angle or quaternion representation, or defined as a weighted sum of angles between corresponding planned and measured fiducial-to-fiducial vectors. In some embodiments, the rotation may be defined as the angle between weighted line-fits of the measured and planned fiducial positions.

User Interface—Association

Figure 6:
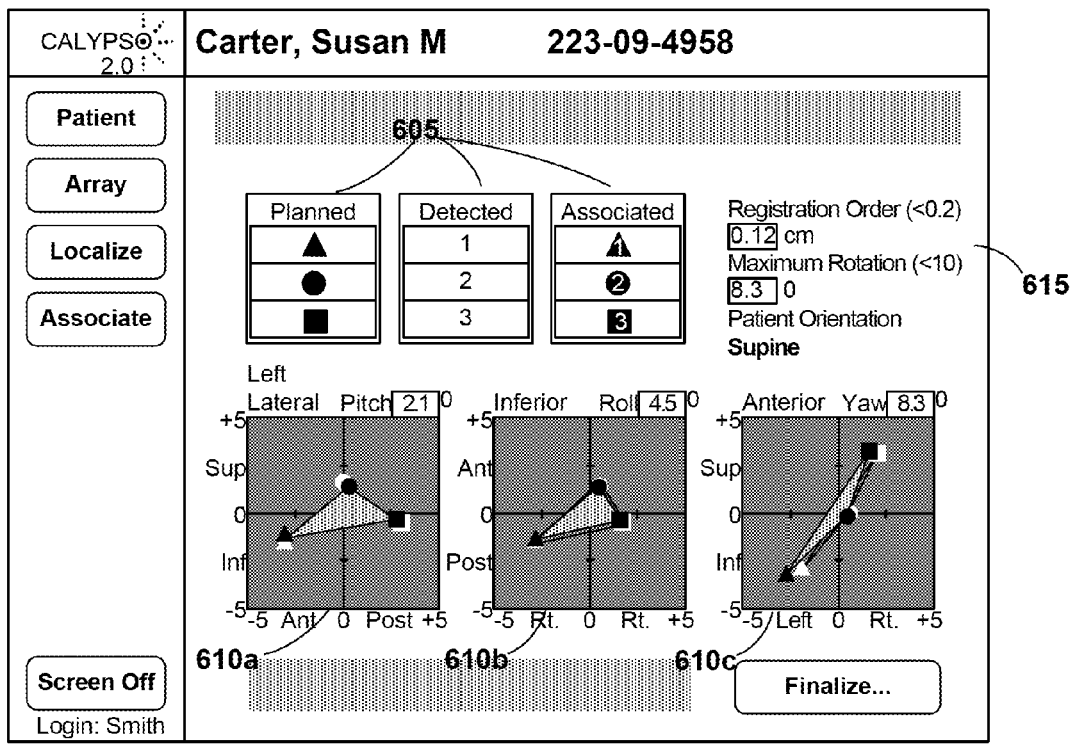
FIG. 6 is a screen shot of a user interface for fiducial association as considered in some embodiments.
Figure 7:
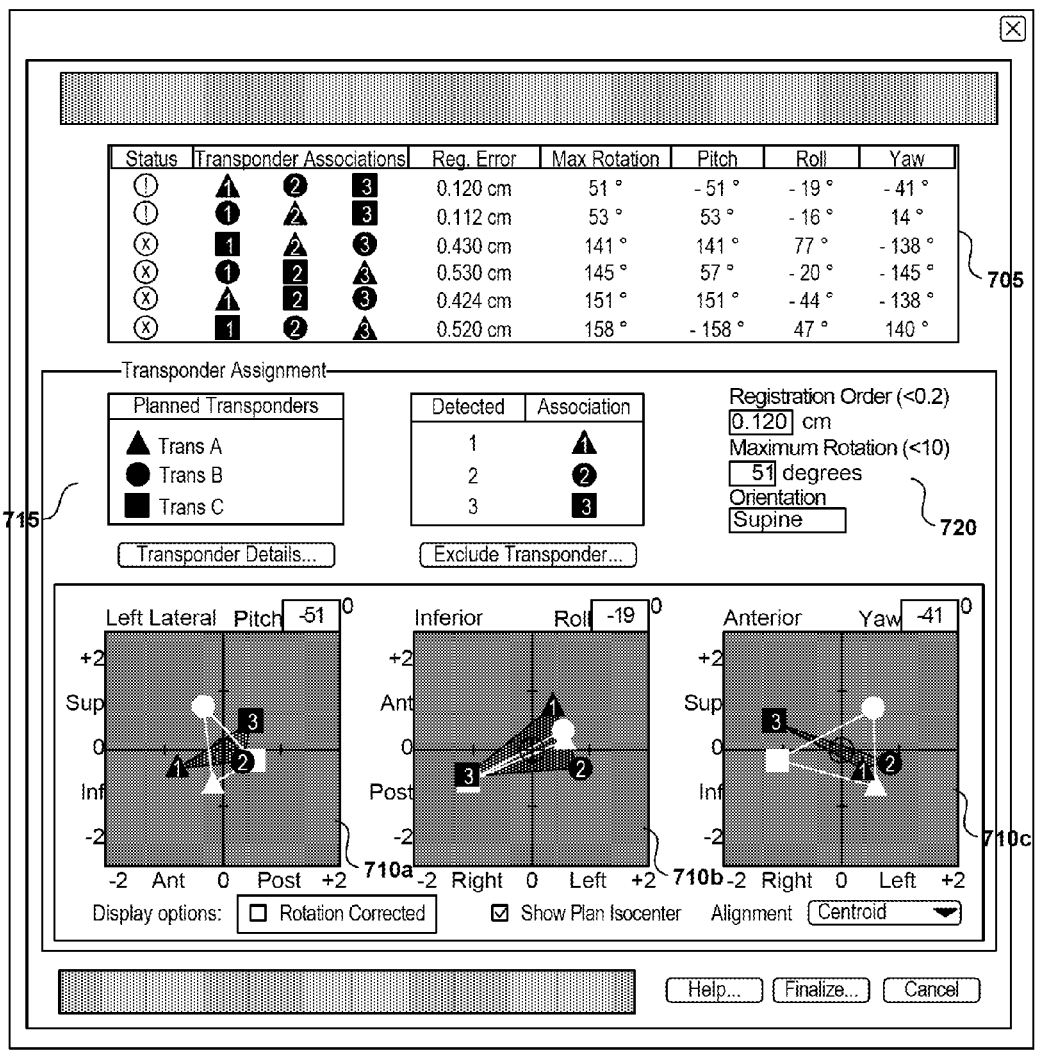
FIG. 7 is a screen shot of a user interface for fiducial association and alignment as considered in some embodiments.
Figure 8:
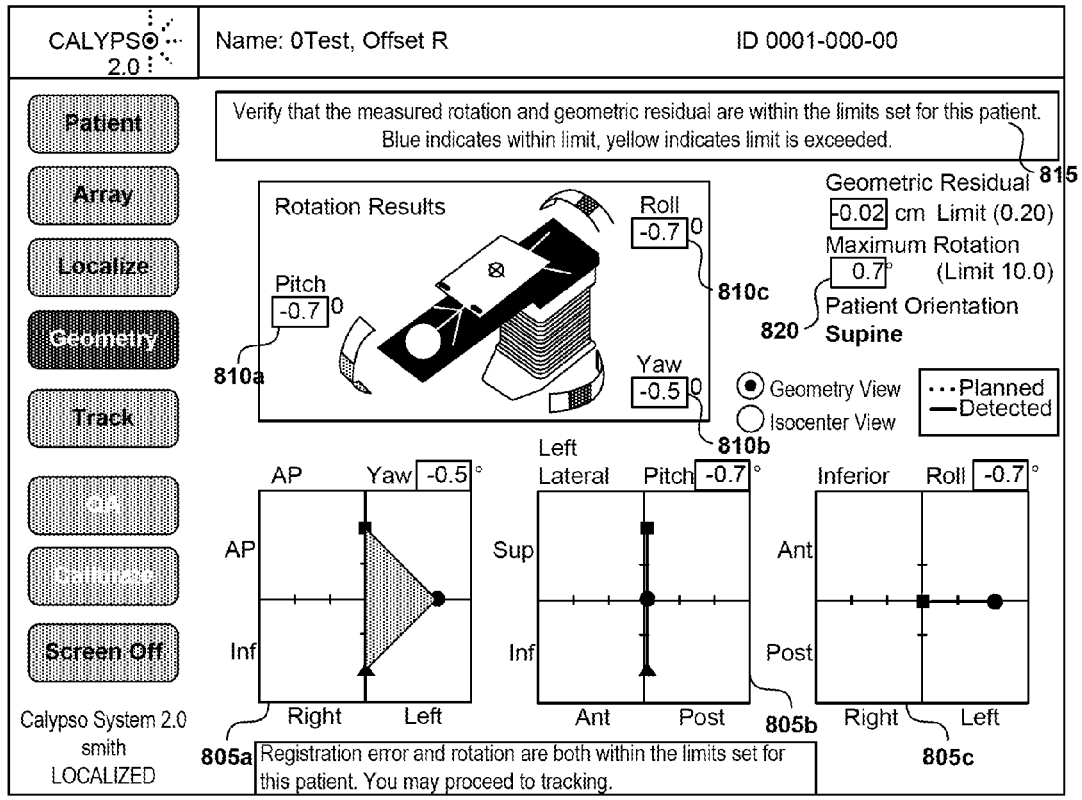
FIG. 8 is a screen shot of a user interface for fiducial geometry verification as considered in some embodiments.

As discussed above, following fiducial association (e.g., following block 430), for each patient treatment session, the fiducial association metrics may be reassessed. The clinician may be apprised of the fiducial conditions using both graphical and numeric geometric information. This per-treatment reassessment may be valuable in determining whether or not the fiducials continue to accurately represent the tumor being treated. FIGS. 6-8 illustrate how the association metrics computed by the initial assessment and/or reassessment may be conveyed to the clinician.

FIG. 6 is a screen shot of a user interface for fiducial association as considered in some embodiments. Different perspective views 610a-c of the plan-to-measured fiducial positions may be provided so that the operator may visualize the relation. An association region 605 may indicate the relationship between detected fiducials, fiducials identified in a plan, and a chosen permutation assignment. Details regarding the correspondence, e.g., the error and rotations required may be indicated in region 615.

FIG. 7 is a screen shot of a user interface for fiducial association and alignment as considered in some embodiments. Different perspective views 710*a-c* of the plan-to-measured fiducial positions may be provided so that the operator may visualize the relation. As indicated, an opaque or translucent surface connecting the fiducial positions may be displayed to facilitate visualization of the correspondence. An association region 705 may indicate the relationship between detected fiducials, fiducials identified in a plan, and a chosen permutation assignment. Details regarding the correspondence, e.g., the error and rotations required may be indicated in region 715.

The results of each of the contemplated permutations may be provided in the region 705. In some embodiments, the user may select the permutation to be used from this region 705. This may allow the user to correct for unique circumstances or developments during treatment. For example, in some embodiments the user has the ability to fully explore assessments for all possible associations of planned and measured data. The user may select a desired association meeting defined constraints. Some embodiments provide a graphical display of select association and corresponding metrics as well as "on-the-fly" ability to exclude a transponder from the association. Possible associations and metrics may be recomputed if a fiducial is excluded. In some embodiments, the 3-dimensional view to that geometry may be aligned to the centroid, or a particular fiducial. This flexibility may aid in better assessing associations. Some embodiments provide the ability to view rotation corrected fiducials to better visualize deformation effects on the association.

FIG. 8 is a screen shot of a user interface for fiducial geometry verification as considered in some embodiments. Different perspective views 805*a-c* of the plan-to-measured fiducial positions may be provided so that the operator may visualize the relation. In some embodiments, one or more views may be presented which the user may manipulate (e.g., zoom, rotate, translate, etc. the view). Details regarding the correspondence, e.g., the error and rotations required may be indicated in region 820.

Instructions may be provided in region 815 to ensure appropriate alignment of the patient based upon the selected fiducial permutation. For example, each of yaw 810*b*, pitch 810*a*, and roll 810*c* adjustments may be indicated, e.g., using color coding to indicate when the patient's orientation is or is not within a desired range for treatment (e.g., yellow or red arrows when out of range and blue or green when in range).

In some embodiments, this assessment, including all the metric values, is provided on every patient session. The assessment may be provided via a 3-dimensional graphical view, facilitating improved geometric understanding. The system may display the planned and measured associations for simultaneous review by the user. The visualization may be used both to allow for potential correction during treatment (such as angle correction) and to provide target location confidence before starting the treatment beam.

Representation System Variations

In some embodiments, the fiducial data may be represented as two, three, four, five, or six dimensional Cartesian positions and/or orientation data (e.g., representation as a quaternion). In some embodiments, the registration algorithm may be a rigid registration, e.g., a rigid Procrustes registration using a p-norm objective function minimization.

In some embodiments, the registration algorithm may be a deformable registration. The deformable registration may employ a structural deformation tissue model.

In the rigid registration, the recommended registration may be one that minimizes an objective function subject to defined constraints (e.g., as discussed above). The objective function may include a rotation metric which may accommodate degenerate geometries.

In some embodiments, the defined constraints include limits on rotation and planned to fiducial error distance. The defined constraints may include limits on registration deformation. In some embodiments, the operator may be presented with a graphical depiction of a selected fiducial association.

The graphical depictions of fiducial associations may be accompanied by their corresponding objective function elements in some embodiments. During patient session reassessment the operator may be presented with a graphical depiction of fiducial association metrics consisting of numeric data and/or a set of orthogonal, two-dimensional, geometric renderings (e.g., as discussed above).

Computer System

Figure 9:
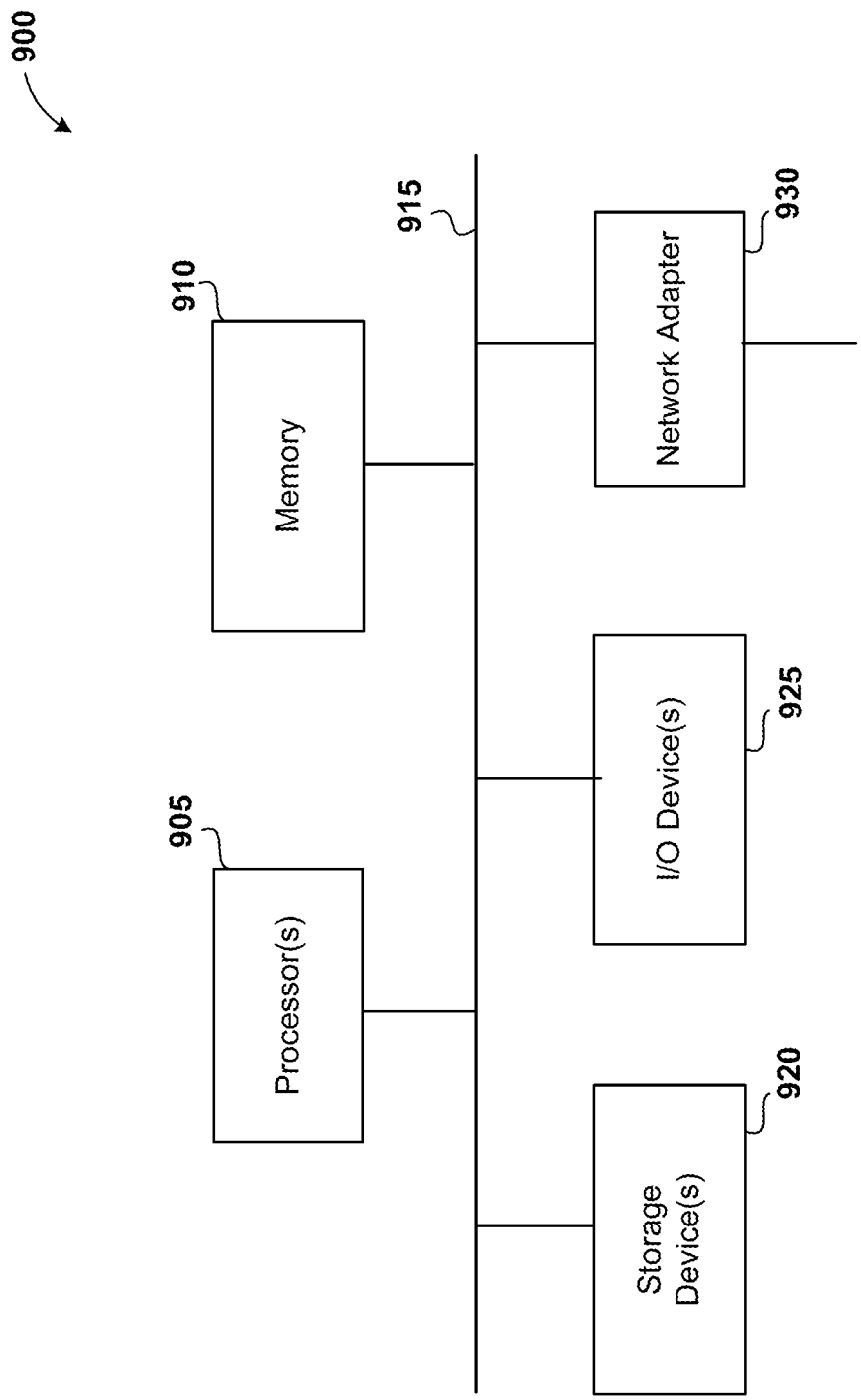
FIG. 9 is a block diagram of a computer system as may be used to implement features of some of the embodiments.

FIG. 9 is a block diagram of a computer system as may be used to implement features of some of the embodiments. The computing system 900 may include one or more central processing units ("processors") 905, memory 910, input/output devices 925 (e.g., keyboard and pointing devices, display devices), storage devices 920 (e.g., disk drives), and network adapters 930 (e.g., network interfaces) that are connected to an interconnect 915. The interconnect 915 is illustrated as an abstraction that represents any one or more separate physical buses, point to point connections, or both connected by appropriate bridges, adapters, or controllers. The interconnect 915, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The memory 910 and storage devices 920 are computer-readable storage media that may store instructions that implement at least portions of the various embodiments. In addition, the data structures and message structures may be stored or transmitted via a data transmission medium, such as a signal on a communications link. Various communications links may be used, such as the Internet, a local area network, a wide area network, or a point-to-point dial-up connection. Thus, computer readable media can include computer-readable storage media (e.g., "non transitory" media) and computer-readable transmission media.

The instructions stored in memory 910 can be implemented as software and/or firmware to program the processor(s) 905 to carry out actions described above. In some embodiments, such software or firmware may be initially provided to the processing system 900 by downloading it from a remote system through the computing system 900 (e.g., via network adapter 930).

The various embodiments introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

Remarks

The above description and drawings are illustrative and are not to be construed as limiting. Numerous specific details are described to provide a thorough understanding of the disclosure. However, in certain instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms may on occasion be used interchangeably.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

What is claimed is:

1. A computer-implemented method, comprising:
    determining, using a sensor assembly of a tracking system, a plurality of measured fiducial positions in or on at least a portion of an animal body, wherein each measured fiducial position generates a location signal at a unique response frequency corresponding to a unique excitation energy from an excitation source of the tracking system;
    determining, using at least one of the tracking system and an imaging apparatus, a plurality of planned fiducial positions associated with a radiation therapy plan;
    determining, using a processor, a first metric correspondence for a first permutation of the plurality of measured fiducial positions in relation to the plurality of planned fiducial positions, wherein the first metric is determined based on a weighted sum of
        distances between the plurality of planned fiducial positions and the plurality of measured fiducial positions,
        a rotation, and
        an offset between a centroid of the plurality of planned fiducial positions and a centroid of the plurality of measured fiducial positions; and
    presenting the first metric to a user via a display.

2. The computer-implemented method of claim 1, wherein the first metric comprises a rotation and registration error assessment metric.

3. The computer-implemented method of claim 1, wherein the distances between the plurality of planned fiducial positions and the plurality of measured fiducial positions comprises a p-norm determination.

4. The computer-implemented method of claim 1, wherein presenting the first metric to the user via the display comprises presenting, to the user, a graphical three-dimensional representation of the plurality of measured fiducial positions and the plurality of planned fiducial positions associated with the plan.

5. The computer-implemented method of claim 4, wherein the graphical three-dimensional representation depicts either the plurality of the measured fiducial positions or the plurality of planned fiducial positions as a surface.

6. The computer-implemented method of claim 1, the method further comprising determining, using the processor, an adjustment associated with the plurality of planned fiducial positions based upon an anticipated deformation in the animal body from a previous measurement of the fiducial positions.

7. A non-transitory computer-readable medium comprising instructions executable by one or more processors to perform a method comprising:
    measuring, using a sensor assembly of a tracking system, a plurality of measured fiducial positions in or on at least a portion of an animal body, wherein each measured fiducial position generates a location signal at a unique response frequency corresponding to a unique excitation energy from an excitation source of the tracking system;
    determining, using at least one of the tracking system and an imaging apparatus, a plurality of planned fiducial positions associated with a radiation therapy plan;
    determining, using the one or more processors, a first metric correspondence for a first permutation of the plurality of measured fiducial positions in relation to the plurality of planned fiducial positions, wherein the first metric is determined based on a weigted sum of at least two of (1) distances between the plurality of planned fiducial positions and the plurality of measured fiducial positions, (2) a rotation, and (3) an offset between a centroid of the plurality of planned fiducial positions and a centroid of the plurality of measured fiducial positions;

determining, using the one or more processors, a second metric correspondence for a second permutation of the plurality of measured fiducial positions in relation to the plurality of planned fiducial positions; and presenting the first metric and the second metric to a user via a display, wherein presenting the first metric and the second metric includes presenting, to the user, a graphical three-dimensional representation of the plurality of measured fiducial positions and the plurality of planned fiducial positions associated with the plan.

8. The non-transitory computer-readable medium of claim 7, wherein the first metric comprises a rotation and registration error assessment metric.

9. The non-transitory computer-readable medium of claim 7, wherein the first metric is determined based on a weighted sum of:
the distances between the plurality of planned fiducial positions and the plurality of measured fiducial positions;
a rotation; and
an offset between a centroid of the plurality of planned fiducial positions and a centroid of the plurality of measured fiducial positions.

10. The non-transitory computer-readable medium of claim 9, wherein the distances between the plurality of planned fiducial positions and the plurality of measured fiducial positions comprises a p-norm determination.

11. The non-transitory computer-readable medium of claim 7, wherein the graphical three-dimensional representation depicts either the plurality of the measured fiducial positions or the plurality of planned fiducial positions as a surface.

12. The non-transitory computer-readable medium of claim 7, the method further comprising determining, using the one or more processors, an adjustment associated with the plurality of planned fiducial positions based upon an anticipated deformation in the animal body from a previous measurement of the fiducial positions.

13. A computer system comprising:
one or more processors; and
at least one memory comprising instructions executable by the one or more processors to cause the computer system to perform a method comprising:
determining a radiation therapy plan prior to measuring a plurality of measured fiducial positions, wherein the radiation therapy plan defines a plurality of planned fiducial positions;
measuring, using a sensor assembly of a tracking system, the plurality of measured fiducial positions in or on at least a portion of an animal body, wherein each measured fiducial position generates a location signal at a unique response frequency corresponding to a unique excitation energy from an excitation source of the tracking system;
determining, using the one or more processors, an adjustment associated with the plurality of planned fiducial positions based upon an anticipated deformation in the animal body from a previous measurement of the fiducial positions difined by a tissue deformation model;
determining, using the one or more processors, a first metric correspondence for a first permutation of the plurality of measured fiducial positions in relation to the plurality of planned fiducial positions;
determining, using the one or more processors, a second metric correspondence for a second permutation of the plurality of measured fiducial positions in relation to the plurality of planned fiducial positions; and
presenting the first metric and the second metric to a user via a display.

14. The computer system of claim 13, wherein the first metric comprises a rotation and registration error assessment metric.

15. The computer system of claim 13, wherein the first metric is determined based on a weighted sum of:
the distances between the plurality of planned fiducial positions and the plurality of measured fiducial positions;
a rotation; and
an offset between a centroid of the plurality of planned fiducial positions and a centroid of the plurality of measured fiducial positions.

16. The computer system of claim 15, wherein the distances between the plurality of planned fiducial positions and the plurality of measured fiducial positions comprises a p-norm determination.

17. The computer system of claim 13, wherein presenting the first metric and the second metric to the user via the display comprises presenting, to the user, a graphical three-dimensional representation of the plurality of measured fiducial positions and the plurality of planned fiducial positions associated with the plan.

18. The computer system of claim 17, wherein the graphical three-dimensional representation depicts either the plurality of the measured fiducial positions or the plurality of planned fiducial positions as a surface.

* * * * *

UNITED STATES PATENT AND TRADEMARK OFFICE
CERTIFICATE OF CORRECTION

PATENT NO. : 9,919,165 B2
APPLICATION NO. : 14/272384
DATED : March 20, 2018
INVENTOR(S) : Edward Vertatschitsch et al.

Page 1 of 1

It is certified that error appears in the above-identified patent and that said Letters Patent is hereby corrected as shown below:

In the Specification

In Column 9, Line 18, after "itself" insert -- . --.

In the Claims

In Column 16, Line 61, in Claim 7, delete "weigted" and insert -- weighted --, therefor.

In Column 18, Line 10, in Claim 13, delete "difined" and insert -- defined --, therefor.

Signed and Sealed this
Fifteenth Day of May, 2018

Andrei Iancu
*Director of the United States Patent and Trademark Office*